(12) United States Patent
Leibfritz

(10) Patent No.: US 10,441,191 B2
(45) Date of Patent: Oct. 15, 2019

(54) MEASURING DEVICE AND A METHOD FOR MICROWAVE-BASED INVESTIGATION

(75) Inventor: Martin Leibfritz, Munich (DE)

(73) Assignee: Rohde & Schwarz GmbH & Co. KG, Munich (DE)

( * ) Notice: Subject to any disclaimer, the term of this patent is extended or adjusted under 35 U.S.C. 154(b) by 1665 days.

(21) Appl. No.: 12/995,989

(22) PCT Filed: Jun. 2, 2009

(86) PCT No.: PCT/EP2009/003925
§ 371 (c)(1),
(2), (4) Date: Feb. 22, 2011

(87) PCT Pub. No.: WO2009/146884
PCT Pub. Date: Dec. 10, 2009

(65) Prior Publication Data
US 2011/0166445 A1    Jul. 7, 2011

(30) Foreign Application Priority Data

Jun. 2, 2008  (DE) .......... 10 2008 026 438
Dec. 16, 2008  (DE) .......... 10 2008 062 484

(51) Int. Cl.
*A61B 5/05*   (2006.01)
*A61B 5/053*  (2006.01)
(Continued)

(52) U.S. Cl.
CPC .......... *A61B 5/0507* (2013.01); *A61B 5/0536* (2013.01); *A61B 5/682* (2013.01);
(Continued)

(58) Field of Classification Search
USPC ........................................................ 600/430
See application file for complete search history.

(56) References Cited

U.S. PATENT DOCUMENTS

| | | |
|---|---|---|
| 5,334,141 A | 8/1994 | Carr |
| 5,704,355 A | 1/1998 | Bridges |
| | (Continued) | |

FOREIGN PATENT DOCUMENTS

| | | |
|---|---|---|
| DE | 30 20 015 A1 | 12/1980 |
| DE | 35 31 893 A1 | 3/1987 |
| | (Continued) | |

OTHER PUBLICATIONS

International Search Report dated Oct. 28, 2009, in corresponding International Application No. PCT/EP2009/003925, filed Jun. 2, 2009.

(Continued)

*Primary Examiner* — Angela M Hoffa
(74) *Attorney, Agent, or Firm* — Christensen O'Connor Johnson Kindness PLLC

(57) ABSTRACT

A measuring device comprises a microwave transmitter, a microwave receiver, at least one antenna, a control device and a dielectric extension. The dielectric extension is disposed between the antenna and an object to be investigated. The control device controls the microwave transmitter and the microwave receiver. The microwave transmitter transmits a microwave signal by means of the antenna and the dielectric extension into the object to be investigated. The object to be investigated scatters the microwave signal. The microwave receiver receives the scattered microwave signal by means of the antenna and the dielectric extension. The length and the dielectric constant of the dielectric extension in this context are dimensioned in such a manner that the object to be investigated is disposed in the remote field of the antenna.

6 Claims, 6 Drawing Sheets

(51) Int. Cl.
  *A61B 5/00* (2006.01)
  *A61B 6/04* (2006.01)
  *A61B 6/00* (2006.01)

(52) U.S. Cl.
  CPC ............ *A61B 6/0435* (2013.01); *A61B 6/502* (2013.01); *A61B 2562/143* (2013.01)

(56) References Cited

U.S. PATENT DOCUMENTS

| | | | | |
|---|---|---|---|---|
| 5,829,437 | A * | 11/1998 | Bridges | 600/430 |
| 6,768,925 | B2 * | 7/2004 | Fenn et al. | 607/101 |
| 7,266,407 | B2 * | 9/2007 | Li et al. | 600/430 |
| 7,427,967 | B2 * | 9/2008 | Hughes | 343/853 |
| 7,647,089 | B2 * | 1/2010 | Bond et al. | 600/430 |
| 7,725,151 | B2 * | 5/2010 | van der Weide | 600/407 |
| 8,050,740 | B2 * | 11/2011 | Davis et al. | 600/430 |
| 8,095,204 | B2 * | 1/2012 | Smith et al. | 600/430 |
| 2004/0077943 | A1 * | 4/2004 | Meaney et al. | 600/430 |
| 2004/0097811 | A1 * | 5/2004 | Smith et al. | 600/448 |
| 2006/0241410 | A1 | 10/2006 | Fang | |
| 2006/0287596 | A1 * | 12/2006 | Johnson et al. | 600/437 |
| 2006/0293597 | A1 * | 12/2006 | Johnson et al. | 600/437 |
| 2007/0060816 | A1 * | 3/2007 | Simpkin | 600/430 |
| 2007/0073144 | A1 * | 3/2007 | Simpkin | 600/430 |
| 2009/0012391 | A9 * | 1/2009 | Simpkin | 600/430 |
| 2009/0024026 | A9 * | 1/2009 | Simpkin | 600/430 |
| 2009/0309786 | A1 * | 12/2009 | Stolpman et al. | 342/25 A |
| 2010/0069744 | A1 * | 3/2010 | Simpkin | 600/425 |
| 2011/0152664 | A1 * | 6/2011 | Leibfritz | 600/407 |
| 2011/0160579 | A1 * | 6/2011 | Leibfritz et al. | 600/431 |

FOREIGN PATENT DOCUMENTS

| | | | |
|---|---|---|---|
| DE | 692 31 294 T2 | 11/2000 | |
| DE | 10 2006 014 230 A1 | 10/2007 | |
| EP | 0694282 A2 * | 1/1996 | ............... A61B 5/00 |
| EP | 0 804 900 A1 | 4/1997 | |
| EP | 1 834 667 A2 | 7/2002 | |
| WO | 2005/053531 A2 | 6/2005 | |
| WO | 2007/112850 A1 | 10/2007 | |

OTHER PUBLICATIONS

English Translation of International Preliminary Report on Patentability dated Mar. 24, 2011, in corresponding International Application No. PCT/EP2009/003925, filed Jun. 2, 2009.

* cited by examiner

MEASURING DEVICE AND A METHOD FOR MICROWAVE-BASED INVESTIGATION

The invention relates to a measuring device and a method for microwave-based investigation.

Antennas, which are distanced by a large air gap from the object to be investigated, are conventionally used for the microwave-based investigation of objects. This serves to achieve remote-field conditions. An influence of the individual object under investigation on the antennas can be avoided in this manner. However, it is disadvantageous that every material transition causes reflections, which interfere with the investigation.

As an alternative, antennas disposed directly on the object to be investigated are used. However, a coupling then occurs between the object under investigation and the antenna. Accordingly, U.S. Pat. No. 5,704,355 discloses a system for detecting breast cancer, which uses an antenna in direct contact with the breast. The additional disadvantage here is the poor accuracy of positioning of the antenna. Accordingly, the breast can slip relative to the antenna during the investigation.

The invention is based on the object of providing a measuring device and a method for microwave-based investigation of objects, which achieve a high quality of investigation and a low cost.

A measuring device according to the invention comprises a microwave transmitter, a microwave receiver, at least one antenna, a control device and a dielectric extension. The dielectric extension is disposed between the antenna and an object to be examined. The control device controls the microwave transmitter and the microwave receiver. By means of the antenna and the dielectric extension, the microwave transmitter transmits a microwave signal into the object to be investigated. The object to be investigated scatters the microwave signal. The microwave receiver receives the scattered microwave signal by means of the antenna and the dielectric extension. The length and the dielectric constant of the dielectric extension in this context are dimensioned in such a manner that the object to be investigated is disposed in the remote field of the antenna. Accordingly, an accurate investigation can be achieved with small dimensions of the measuring device.

The dielectric extension advantageously comprises a dielectric constant of $\varepsilon > 2$, preferably of $\varepsilon > 3$, by particular preference of $\varepsilon > 4$. The extension advantageously comprises a length from 20 cm to 120 cm, preferably from 30 cm to 100 cm, by particular preference from 40 cm to 80 cm. Particularly small dimensions of the measuring device can therefore be achieved.

The dielectric extension advantageously provides a laterally disposed microwave absorber. In this manner, interference through lateral scattering of the microwave signals is avoided.

By preference, the microwave absorber is made from a strongly attenuating, non-reflecting material. Accordingly, interference from lateral scattering of the microwave signals can be avoided with small dimensions of the measuring device.

The object to be investigated is preferably a breast of a female patient. The breast is preferably disposed between the patient and the extension. By preference, substantially no air is disposed between the breast and the extension. Accordingly, a flat breast, largely homogenous in its thickness is achieved. Moreover, a low-reflection transition of the radiation is achieved in this manner. A high accuracy of the measurement is therefore achieved, especially for the detection of breast cancer.

An alternative measuring device according to the invention comprises a microwave transmitter, a microwave receiver, at least one antenna arrangement and a control device. The first antenna arrangement is attached to an object to be investigated by means of adhesion, especially gluing or clamping. The control device controls the microwave transmitter and the microwave receiver. The microwave transmitter transmits the microwave signal by means of the first antenna arrangement into the object to be investigated. Alternatively or additionally, the microwave receiver receives the microwave signal by means of the first antenna arrangement. Reflections at the transition between the air and the object under investigation are avoided in this manner. Accordingly, a high accuracy is possible.

The measuring device preferably contains at least one second antenna arrangement. The first antenna arrangement and the second antenna arrangement are preferably individual antennas or antenna arrays. Accordingly, a further increase in accuracy can be achieved.

The microwave transmitter preferably transmits a microwave signal into the object to be investigated by means of the first antenna arrangement. The microwave receiver preferably receives the scattered signal by means of the second antenna arrangement. Alternatively, the microwave transmitter transmits a microwave signal into the object to be investigated by means of the second antenna arrangement. The microwave receiver then preferably receives the scattered signal by means of the first antenna arrangement. In this manner, complex signal processing for the separation of signals transmitted by a single antenna and received by the same antenna can be avoided.

The second antenna arrangement preferably occupies in succession several positions relative to the object to be investigated. Accordingly, a high-sensitivity resolution can be achieved.

In the following section, the invention is described by way of example with reference to the drawings, in which advantageous exemplary embodiments of the invention are presented. The drawings are as follows.

Figure 1:
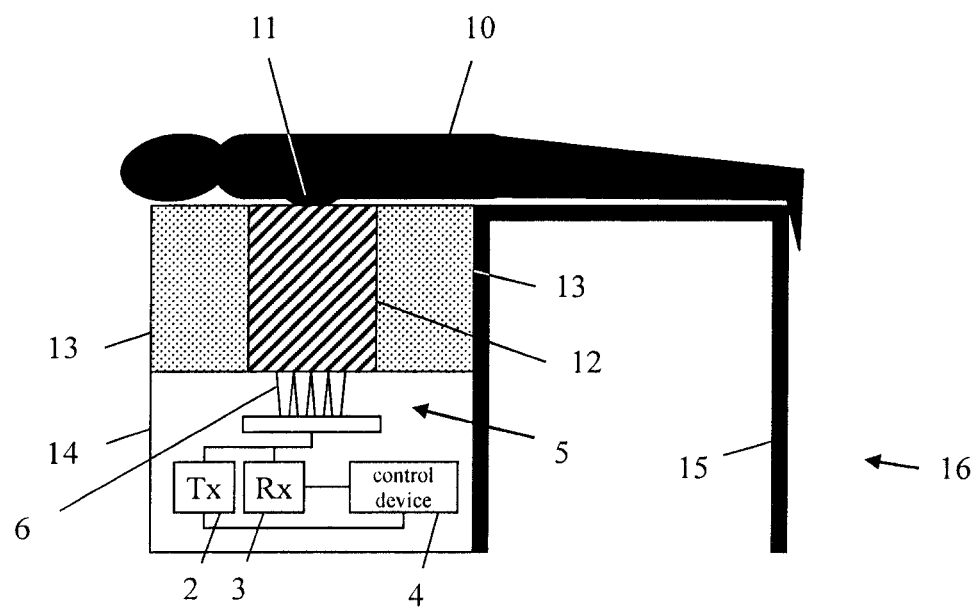
FIG. 1 shows a first exemplary embodiment of the measuring device according to the invention.
Figure 2:
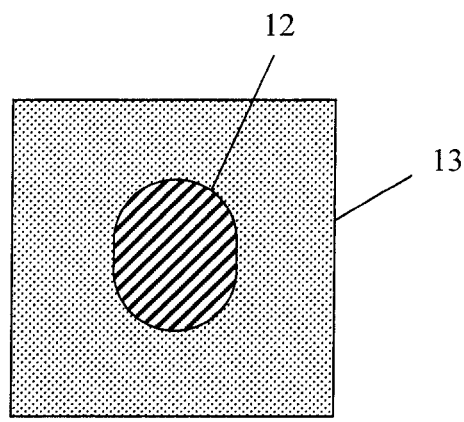
FIG. 2 shows a detail of the first exemplary embodiment of the measuring device according to the invention.

The structure and functioning of the device of the invention according to claim 1 is initially presented with reference to FIGS. 1-2. With reference to FIGS. 3-8, the structure and functioning of the device of the invention according to claim 6 is then explained. Finally, the functioning of various exemplary embodiments of the method according to the invention is presented by means of FIGS. 9-10. In some cases, the presentation and description of identical elements in similar drawings has not been repeated.

FIG. 1 shows a first exemplary embodiment of the measuring device according to the invention. A patient 10 is lying in an investigation station 16. In addition to a table 15, the investigation station 16 comprises a housing 14, a dielectric extension 12 and an absorber 13. The housing 14 is disposed below the dielectric extension 12 and the absorber 13. The table 15 is disposed alongside the housing 14, the dielectric extension 12 and the absorber 13. The dielectric extension 12 and the absorber 13 in this context are shown in a cross-sectional presentation.

The breast 11 of the patient 10 is disposed between the rest of her body and the dielectric extension 12 above a first end of the dielectric extension. In this context, the breast 11 is compressed by the body weight of the patient 10. This leads to a largely flat, uniformly thick shape of the breast 11. In this manner, a correction calculation, which eliminates reflections at the surface of the breast, can be implemented in a simplified manner. An upright seated position of the patient 10 or a lying position with the extension 12 placed above are also possible.

The housing 14 contains a microwave transmitter 2, a microwave receiver 3, a control device 4 and an antenna array 5. In this context, the antenna array 5 comprises a plurality of individual antennas 6.

The breast 11 of the patient 10 in this exemplary embodiment is the object to be investigated. The control device 4 controls the microwave transmitter 2 in such a manner that the latter transmits a microwave signal by means of the antenna array 5 into the object to be investigated. In this context, the microwave signal is transmitted from the antenna array 5 directly into the extension 12. The extension 12 here provides a high dielectric constant and a low attenuation. In this manner, the effective wavelength of the microwave signal is reduced within the dielectric extension 12. Accordingly, the microwave signal runs through a higher number of wavelengths while it passes through the extension than is the case in a passage through the air. Accordingly, decoupling of the antenna array 5 from the object to be investigated is achieved even at a short distance. That is to say, the antenna properties are not influenced by the properties of the object to be investigated. A decoupling of this kind occurs when remote-field conditions predominate. This is the case, when the microwave signal has covered at least six wavelengths between the antenna 6 and the breast 11.

Using the extension 12 allows the use of high-frequency microwave radiation, without the need to preserve a large distance between the antenna and the object to be investigated.

To avoid interference from microwave signals reflected from the edges of the extension 12, the extension 12 is surrounded by an absorber 13. In this context, the absorber 13 is made from a microwave-absorbing material.

Additional interference from restrictions of the microwave signal at the transition with the air is avoided through the direct contact of the breast 11 on the dielectric extension 12.

The microwave signal is scattered by the object to be investigated, here the breast 11. A part of the scattered microwave signal is scattered through the extension 12 back to the antenna array 5. The microwave receiver 3 is controlled by the control device 4 in such a manner that the former receives the microwave signal scattered back.

In order to achieve as high-sensitivity a resolution as possible within the object to be investigated, different transmission positions and reception positions are used. In this exemplary embodiment, this is achieved by using different individual antennas 6 of the antenna array 5. Finally, the control device 4 determines from the received microwave signals a microwave tomography of the object to be investigated.

FIG. 2 presents a detail of the first exemplary embodiment of the measuring device according to the invention. The drawing shows a sectional view of the dielectric extension 12 and of the absorber 13. In this case, the section passes through the horizontal plane.

The form of the extension 12 adapted to the object to be investigated, here, the breast 11 of the patient 10, is clearly recognisable. The absorber 13 completely encloses the extension 12 in the horizontal plane. The absorber 13 provides a thickness, which substantially corresponds to the smallest radius of the extension 12. In this manner, a secure absorption of the microwave radiation emitted from the extension 12 is achieved. Interference through reflections is therefore reduced.

Figure 3:
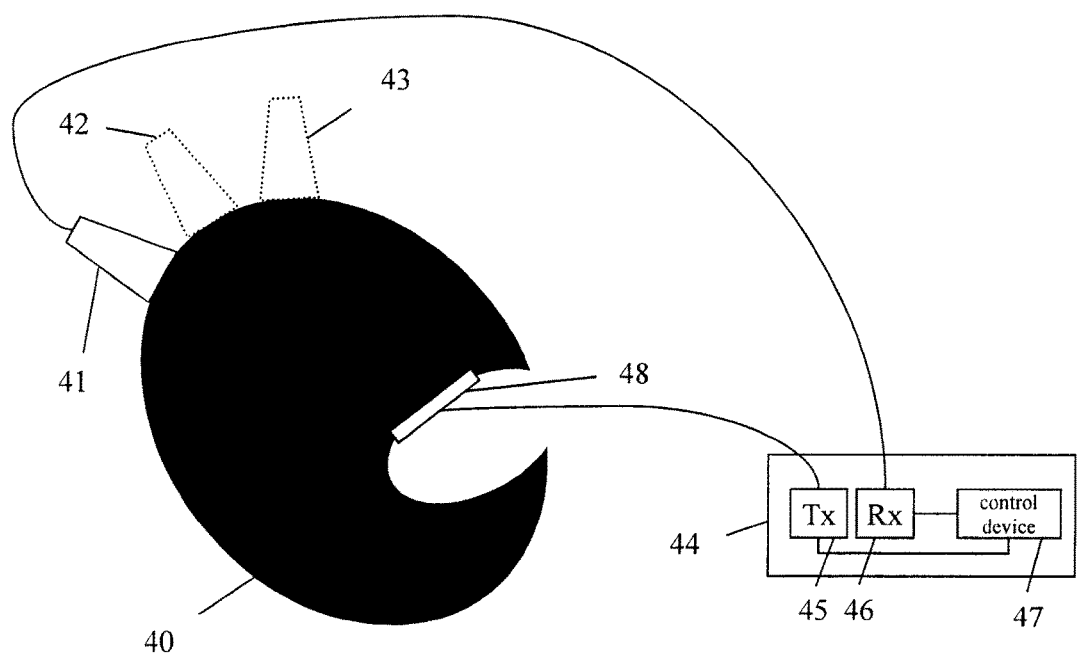
FIG. 3 shows a second exemplary embodiment of the measuring device according to the invention.

FIG. 3 shows a second exemplary embodiment of the measuring device according to the invention. A housing 44 contains a microwave transmitter 45, a microwave receiver 46 and a control device 47. The control device 47 controls both the microwave transmitter 45 and also the microwave receiver 46. The microwave transmitter 45 is connected to an antenna arrangement 48. The antenna arrangement 48 is disposed in a patient's mouth. It is fixed, for example, by means of an adhesive to the palate in the patient's head 40. In this context, the antenna arrangement 48 is at least partially flexible and can accordingly be adapted to the surface of the palate. The microwave receiver 46 is connected to an antenna 41. The antenna 41 here is in direct contact with the outer side of the patient's head 40. The object to be investigated here is the patient's head 40.

In order to implement an investigation, the control device 47 controls the microwave transmitter 45 in such a manner that it transmits a microwave signal by means of the antenna arrangement 48 into the patient's head 40. The microwave signal is scattered by the object to be investigated. The scattered microwave signal is received by the microwave receiver 46 by means of the antenna 41 and rerouted to the control device 47. The antenna 41 adopts several different positions 42, 43 in succession. In this manner, a high-sensitivity resolution is achieved in the investigation. From the scattered signals, the control device 47 determines an at least two-dimensional microwave tomography of the object to be investigated. As an alternative to a re-positioning of the antenna 41, an antenna array can be used.

In this exemplary embodiment, it is particularly advantageous that only very few reflections occur. This is achieved by avoiding air gaps between the antenna arrangement 48 and the patient's head 40 and between the patient's head 40 and the antenna 41. However, the disadvantage with this exemplary embodiment is that, because of the small distance, a coupling of the antenna arrangement 48 with the patient's head, and of the antenna 41 with the patient's head 40 occurs. Accordingly, a complex calibration is required for every different object to be investigated, that is to say, for every different patient.

As an alternative to the transmission of the microwave signal by means of the antenna arrangement 48 and the reception of the microwave signal by the antenna 41, a reverse procedure is also possible. In this context, the transmission positions are changed through displacement of the antenna 41 to the several positions 42, 43, and the high-sensitivity resolution is achieved in this manner.

Figures 4, 5:
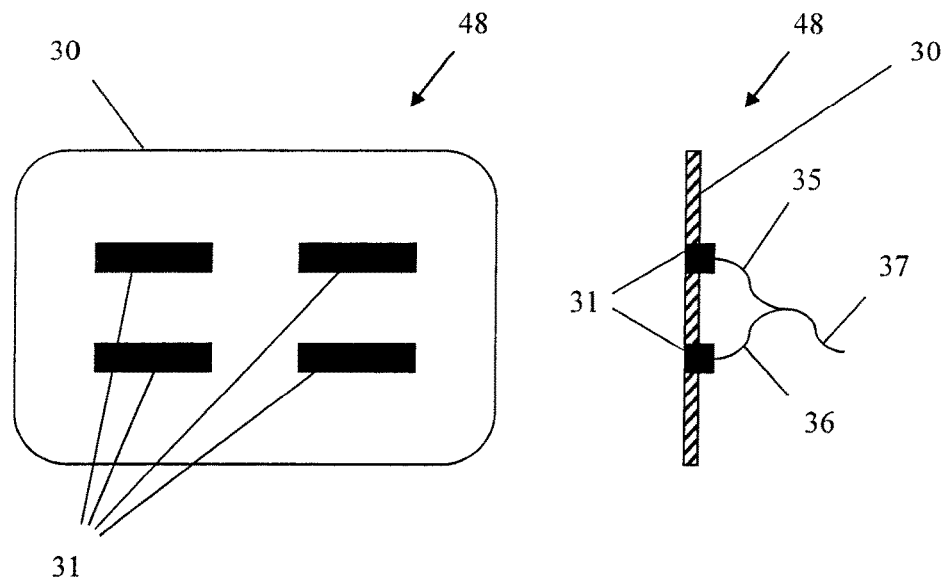
FIG. 4 shows a first detail of the second exemplary embodiment of the measuring device according to the invention.
FIG. 5 shows a second detail of the second exemplary embodiment of the measuring device according to the invention.

FIG. 4 provides a first detail of the second exemplary embodiment of the measuring device according to the invention. The underside, that is to say, the side of the antenna arrangement 48 attached to the palate in FIG. 3, is illustrated here. It contains a flexible carrier 30 and four antenna elements 31. The antenna elements 31 in this context are conductive strips on the underside of the flexible carrier 30.

FIG. 5 shows a second detail of the second exemplary embodiment of the measuring device according to the invention. Here, the antenna arrangement 48 is shown in a lateral sectional view. The antenna elements 31 are connected on the upper side of the flexible carrier 30 to signal lines 35, 36, which are bundled to form a common signal line 37.

Figure 6:
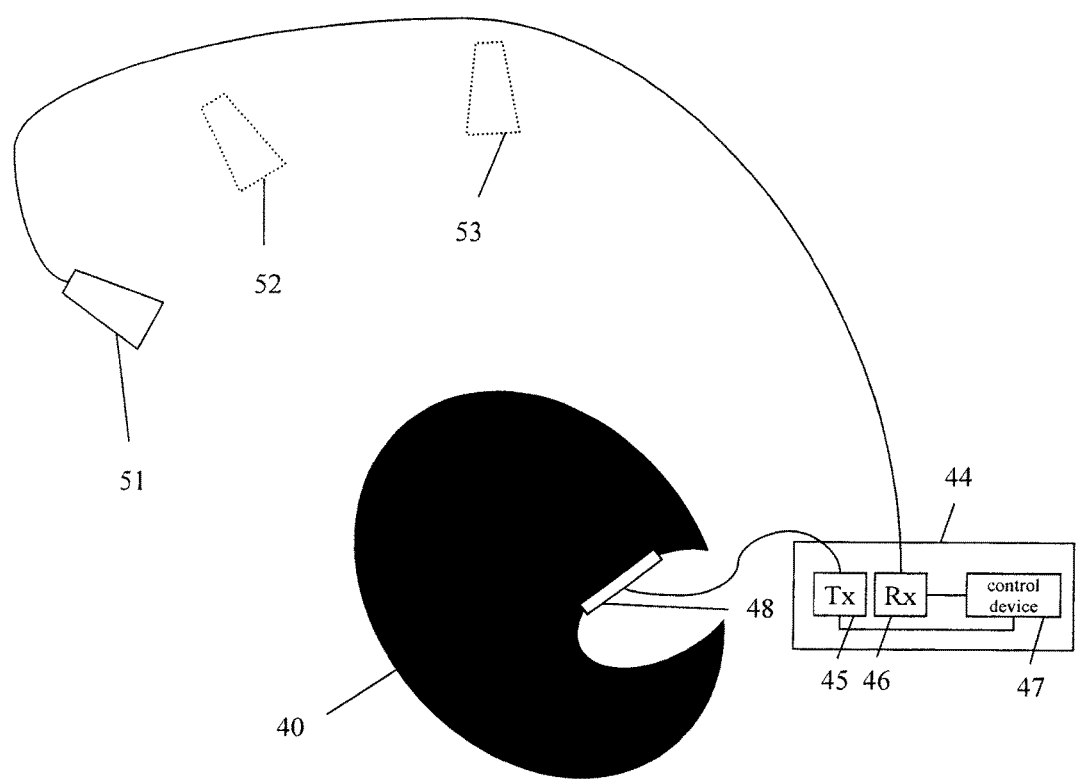
FIG. 6 shows a third exemplary embodiment of the measuring device according to the invention.

FIG. 6 shows a third exemplary embodiment of the measuring device according to the invention. In order to remove the difficulties caused by the coupling of the antenna 41 and the patient's head 40 explained with reference to FIG. 3, the antenna 51, which corresponds to the antenna 41 from FIG. 3, has not been positioned directly on the patient's head 40. Instead, the antenna 51 provides a spacing distance relative to the patient's head 40. In this context, the spacing distance is selected in such a manner that remote-field conditions predominate.

Otherwise, the exemplary embodiment presented here corresponds to the exemplary embodiment presented in FIG. 3.

Figure 7:
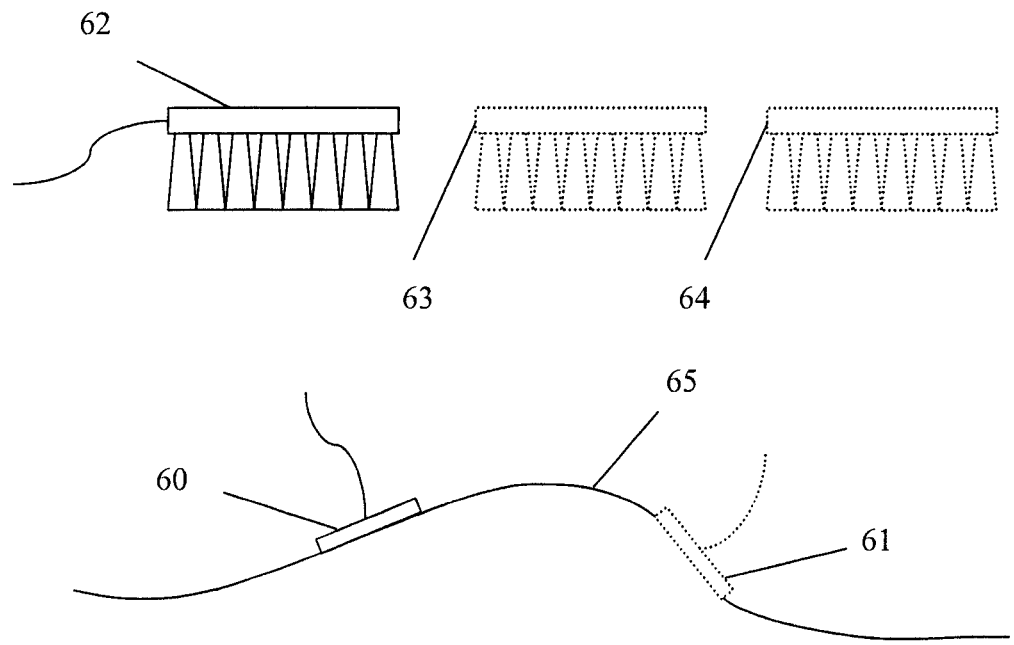
FIG. 7 shows a fourth exemplary embodiment of the measuring device according to the invention.

FIG. 7 shows a fourth exemplary embodiment of the measuring device according to the invention. The object to be investigated is once again a human breast 65. An antenna arrangement 60 is attached to the breast 65, for example, by gluing. An antenna array 62 is disposed at a spacing distance relative to the breast 65, which guarantees remote-field conditions. In order to implement an investigation, a microwave signal is transmitted into the breast 65 by means of the antenna arrangement 60. The microwave signal is scattered by the breast 65. The scattered microwave signal is received by the antenna array 62. A microwave tomography of the breast 65 is determined from the received microwave signal by a control device, as presented in FIG. 1, FIG. 3 and FIG. 6. In order to increase the high-sensitivity resolution further, the antenna array 62 is brought in succession into different positions 63, 64. A further increase in the high-sensitivity resolution is achieved by bringing the antenna arrangement 60 to the additional position 61 after the investigation at its original position. A high-sensitivity resolution is achieved through the multiplicity of reception positions and transmission positions.

Through the direct positioning of the antenna arrangement 60 on the breast 65, very low interference through reflections on the skin is achieved. A reversal of the transmission direction is also possible with this exemplary embodiment. In this manner, the antenna array 62 is used for transmitting the microwave signal, while the antenna arrangement 60 is used for receiving the microwave signal.

Figure 8:
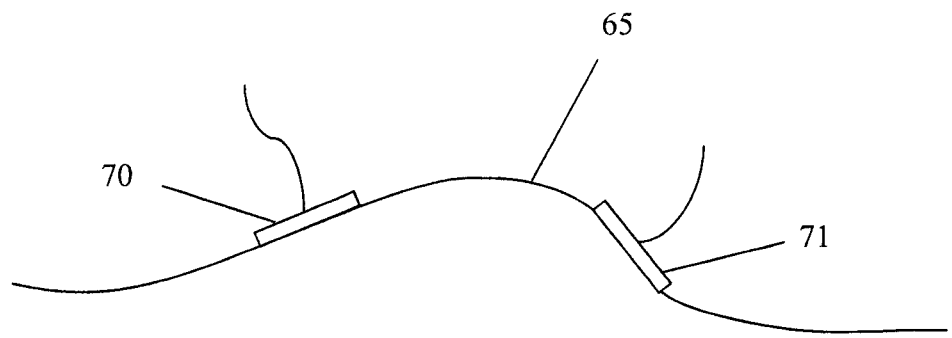
FIG. 8 shows a fifth exemplary embodiment of the measuring device according to the invention.

In FIG. 8, a fifth exemplary embodiment of the measuring device according to the invention is presented. The exemplary embodiment presented here corresponds in part with the exemplary embodiment presented in FIG. 7. The antenna arrangement 70 corresponds to the antenna arrangement 60 from FIG. 7. Instead of an antenna array 62 from FIG. 7, a second antenna arrangement 71 is used. In this context, the second antenna arrangement 71 is glued like the first antenna arrangement 70 to the breast 65. For the implementation of an investigation, a microwave signal is transmitted by means of the first antenna arrangement 70 into the breast 65. The microwave signal is scattered by the breast 65. The scattered microwave signal is received by the second antenna arrangement 71. A high-sensitivity resolution is achieved in that every antenna element 70, 71 comprises several individual antennas. An additional increase in the high-sensitivity resolution is possible through the use of additional antenna arrangements. A re-positioning of the only two antenna arrangements 70, 71 also achieves an increase in the high-sensitivity resolution. However, every re-positioning is associated with a positioning inaccuracy.

With this exemplary embodiment also, a control device determines a microwave tomography from the received microwave signals, as in FIG. 1, FIG. 3 and FIG. 6. Here also, a reversal of the direction of transmission is possible. Accordingly, the antenna arrangement 71 can also be used for transmitting the microwave signal, while the antenna arrangement 70 is used for receiving the scattered microwave signal.

Figure 9:
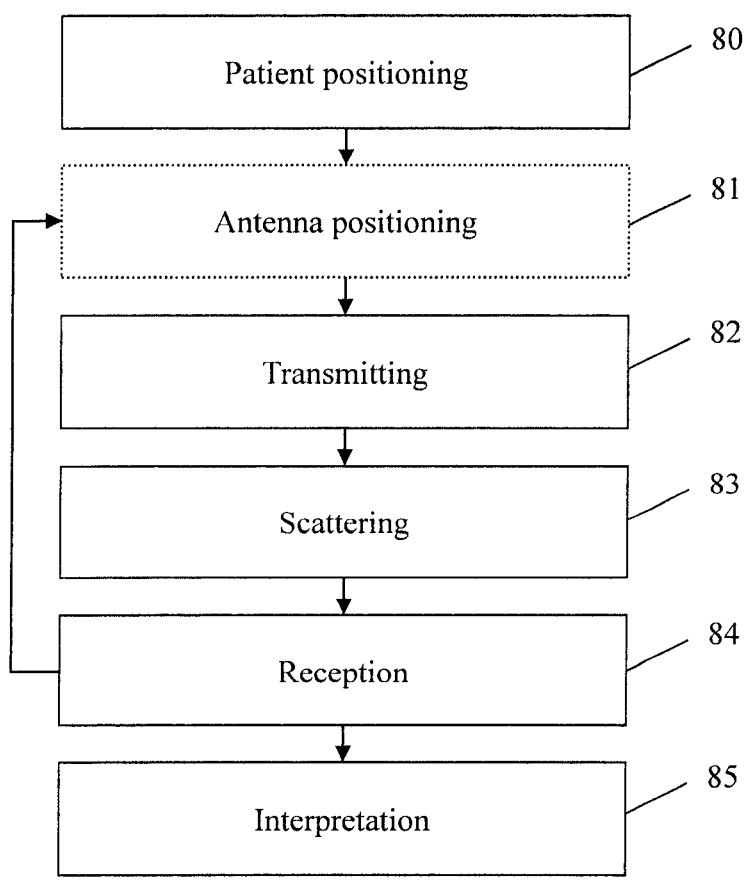
FIG. 9 shows a flow chart of a first exemplary embodiment of the method according to the invention.

FIG. 9 shows a flow chart of a first exemplary embodiment of the method according to the invention. In a first step 80, the object to be investigated, here, a patient, is positioned. In this context, it is brought into direct contact with the dielectric extension described in detail with reference to FIGS. 1-2. In an optional second step 81, the antenna is positioned relative to the object. This step is relevant in the case of movable individual antennas. With the use of an antenna array, the high-sensitivity resolution can be increased by positioning the antenna array at different positions. In a third step 82, a microwave signal is transmitted into the object to be investigated. In a fourth step 83, the microwave signal is scattered by the object to be investigated. In a fifth step 84, the scattered microwave signal is received.

The second step 81 to the fifth step 84 are repeated for different locations within the object to be investigated. The optional second step 81 can be omitted, if the high-sensitivity resolution is achieved through the use of different individual antennas of an antenna array. After the completion of the measurements at all of the locations to be investigated within the object to be investigated, a microwave tomography of the object to be investigated is determined in a sixth step 85.

Figure 10:
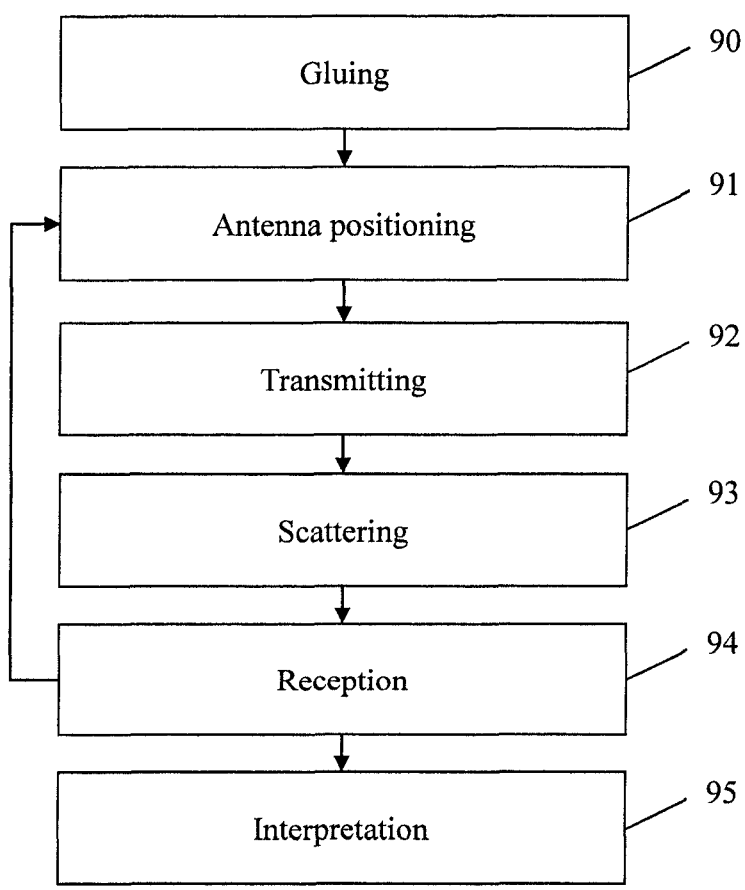
FIG. 10 shows a flow chart of a second exemplary embodiment of the method according to the invention.

FIG. 10 presents a second exemplary embodiment of the method according to the invention. In a first step 90, an antenna arrangement is attached by means of gluing to the object to be investigated. In a second step 91, the object to be investigated, here, a patient, is positioned relative to further antennas or respectively to an antenna array. In a third step 92, a microwave signal is transmitted into the object to be investigated by means of the antenna arrangement. In a fourth step 93, the microwave signal is scattered by the object to be investigated. In a fifth step 94, the scattered microwave signal is received by the further antennas or respectively by the antenna array.

The second step 91 to the fifth step 94 are repeated for several different locations within the object to be investigated. In this manner, an improved high-sensitivity resolution is achieved. A movement of the further antennas or of the antenna array relative to the object to be investigated can be omitted, if the high-sensitivity resolution is achieved through the use of several different individual antennas of an antenna array. In a sixth step 95, a microwave tomography is produced by means of the received microwave signals.

A reversal of the signal direction is also possible with this exemplary embodiment. For example, the microwave signal can also be transmitted by the further antennas or respectively by the antenna array and received by the antenna arrangement glued in place. The objects to be investigated can be any required objects, especially living or dead human or animal tissue.

The invention is not restricted to the exemplary embodiment presented. As already mentioned, different objects can be investigated. The use of different numbers of antennas is also possible. All of the features described above or illustrated in the drawings can be combined with one another advantageously as required within the framework of the invention.

The invention claimed is:

1. A measuring device, comprising: a microwave transmitter; a microwave receiver; at least one antenna; a control device configured to control the microwave transmitter and the microwave receiver; and a dielectric extension adapted to be disposed between the antenna and an object to be investigated to electrically decouple the antenna from the object to be investigated, wherein the microwave transmitter is configured to transmit a microwave signal by the antenna and the dielectric extension into the object to be investigated, wherein the object to be investigated is capable of scattering the microwave signal, wherein the microwave receiver is configured to receive the scattered microwave signal by the antenna and the dielectric extension, wherein the dielectric extension has a length of 40 cm to 80 cm and has a dielectric constant of $\varepsilon>4$ such that the object to be investigated is disposed in a remote field of the antenna, wherein the remote field of the antenna is reached after a travel by the microwave signal through the dielectric extension of six wavelengths, wherein the object to be investigated is a breast of a female patient, the breast being disposed at one end of the dielectric extension such that substantially no air is disposed between the breast and the dielectric extension, and wherein the measuring device is arranged so that the breast of a patient is disposed between the rest of the body and the dielectric extension above a first end of the dielectric extension, and wherein the measuring device is being arranged so that the breast of the patient is compressed by the body weight of the patient, leading to a largely flat, uniformly thick shape of the breast.

2. The measuring device according to claim 1, wherein a microwave absorber surrounds the dielectric extension.

3. The measuring device according to claim 2, wherein the microwave absorber comprises a strongly attenuating, non-reflecting material.

4. A method for investigating an object with a microwave transmitter, a microwave receiver, at least one antenna, a control device and a dielectric extension, wherein the microwave transmitter and the microwave receiver are controlled by the control device, the method comprising:

transmitting the microwave signal by the microwave transmitter by the antenna;

extending the effective path of the microwave signal by the dielectric extension, wherein the dielectric extension has a length of 40 cm to 80 cm and has a dielectric constant of $\varepsilon>4$ such that the object to be investigated is disposed in a remote field of the antenna, and wherein the remote field of the antenna is reached after a travel by the microwave signal through the dielectric extension of six wavelengths;

scattering of the microwave signal by the object to be investigated; and receiving the scattered microwave signal by the microwave receiver by the antenna, wherein the object to be investigated is a breast of a female patient, the breast being disposed at one end of the dielectric extension such that substantially no air is disposed between the breast and the dielectric extension, and wherein the measuring device is arranged so that the breast of a patient is disposed between the rest of the body and the dielectric extension above a first end of the dielectric extension, and wherein the measuring device is being arranged so that the breast of the patient is compressed by the body weight of the patient, leading to a largely flat, uniformly thick shape of the breast.

5. The method according to claim 4, wherein the microwave radiation leaving the dielectric extension is absorbed by a microwave absorber surrounding the dielectric extension.

6. The method according to claim 5, wherein the microwave absorber comprises a strongly attenuating, non-reflecting material.

* * * * *